United States Patent [19]

Dougherty et al.

[11] Patent Number: 4,542,231

[45] Date of Patent: Sep. 17, 1985

[54] STABILIZED ETHYLENICALLY UNSATURATED ORGANIC COMPOSITIONS

[75] Inventors: Edward F. Dougherty, League City; Mark O. Scates, Pearland, both of Tex.

[73] Assignee: Celanese Corporation, New York, N.Y.

[21] Appl. No.: 510,870

[22] Filed: Jul. 5, 1983

[51] Int. Cl.[4] .................... C07C 67/62; C07C 103/33; C07C 7/20
[52] U.S. Cl. ........................................ 560/4; 562/598; 564/4; 585/3; 585/4; 585/5; 585/435
[58] Field of Search ................ 560/4; 562/598; 564/4; 585/3, 4, 5, 435

[56] References Cited

U.S. PATENT DOCUMENTS

| | | | |
|---|---|---|---|
| 2,143,941 | 1/1939 | Crawford | 560/4 |
| 2,154,389 | 4/1939 | Stoesser | 560/4 X |
| 2,259,513 | 10/1941 | Barnes | 560/4 X |
| 3,356,663 | 12/1967 | Loversidge et al. | 560/4 |
| 3,959,358 | 5/1976 | Jurisch | 560/4 X |

*Primary Examiner*—Natalie Trousof
*Assistant Examiner*—Vera C. Clarke
*Attorney, Agent, or Firm*—L. I. Grim; M. Turken

[57] ABSTRACT

New and improved compositions are described of ethylenically unsaturated organic compounds capable of addition polymerization stabilized from unintentional or premature polymerization in the liquid phase by the addition of the combination cerium compounds which are soluble in the ethylenically unsaturated organic compounds and phenolic type inhibitors.

16 Claims, No Drawings

STABILIZED ETHYLENICALLY UNSATURATED ORGANIC COMPOSITIONS

This invention relates to compositions of ethylenically unsaturated organic compounds stabilized from unintentional or premature polymerization in the liquid phase. More specifically the compositions of this invention comprise ethylenically unsaturated organic compounds containing a combination of a stabilizing amount of a cerium compound which is soluble in the ethylenically unsaturated organic compounds and phenolic type inhibitors.

BACKGROUND OF THE INVENTION

Ethylenically unsaturated organic compounds, capable of addition polymerization, such as acrylic acid, methacrylic acid, methacrylic esters, acrylate esters and the like are widely used in the production of homopolymers and copolymers. These homopolymers and copolymers, produced readily through the polymerization of the available double bonds of the organic compounds, are widely used in paints, coatings, lacquers and the like. The olefinic activity of the ethylenically unsaturated organic compounds, makes the polymerized products highly useful for many purposes. On the other hand, the olefinic activity poses a problem of unintentional or premature polymerization promoted by light and heat. This tendency is exhibited on storage, shipping or even during purification of these polymerizable unsaturated compounds where distillation at higher temperatures are involved.

It is the practice to employ stabilizers to inhibit the setting of polymerizable ethylenically unsaturated organic compounds. For example, in the stabilization of acrylic acid and other unsaturated compounds, inhibitors commonly used are phenothiazine, methylene blue, hydroquinone in the presence of oxygen, N,N'-diphenyl-p-phenylenediamine, the monomethyl ether of hydroquinone and the like. The amount of inhibitor customarily used is sufficient to prevent hazardous polymerization even after prolonged storage at normal temperatures. For acrylic acids the amounts commonly used for storage include: phenothiazine, about 200 parts per million; methylene blue 0.5–1%; hydroquinone, 0.1%; N,N'-diphenyl-p-phenylenediamine, 0.05%; and the monomethyl ether of hydroquinone, 0.05–0.1%. Removal or reduction in amounts of these stabilizers from the ethylenically unsaturated organic monomer product, prior to the polymerization reaction, is generally carried out by distillation in instances at reduced pressures. Even at low pressure, distillation of these monomers is difficult because polymer forms readily. During the distillation the liquid phase in the distillation unit should contain a liquid phase nonvolatile inhibitor and the column and condenser should contain a volatile inhibitor such as nitric oxide to prevent the undesired or premature polymerization of the ethylenically unsaturated organic monomer product.

It is not generally known to use a metal additive in combination with phenolic inhibitors to prevent undesirable polymerization of ethylenically unsaturated organic compounds. In *Chemical Abstracts*, Vol. 74, 1971, 112642V, a Japanese patent (No. 70-35,285) filed June 1, 1967, assigned to Nippon Kayaku Co., Ltd. describes the mixture of chromium acetate with hydroquinone as a satisfactory inhibitor for acrylic and methacrylic acid. In Japanese patent publication No. 51-98211, filed Feb. 19, 1975, assigned to Sumitomo Chemical Co., Ltd., the combination of manganese salt and phenolic type inhibitors provide satisfactory stabilization of acrylic acid. The use of cerium is not known as an inhibitor alone or in combination with other inhibitors as a stabilizer for the polymerizable ethylenically unsaturated organic compounds.

THE INVENTION

By this invention, a new and improved ethylenically unsaturated organic compound capable of addition polymerization is provided which is stabilized from unintentional or premature polymerization in the liquid phase by the addition of the combination in stabilizing amounts of a cerium compound which is soluble in the ethylenically unsaturated organic compounds and phenolic type inhibitors. The stabilization of the ethylenically unsaturated organic compound is achieved by the addition of cerium of at least about 0.00001 weight percent (0.1 part per million) to as high as 0.5 weight percent (5000 parts per million) of the total weight of the compound or higher in combination with 0.0001 (one part per million) weight percent to about 0.5 weight percent (5000 parts per million) of the total weight of the compound of phenolic type stabilizers. At higher amounts, satisfactory stabilization occurs but the excess amount of inhibitor is not necessary.

The preferred amounts of soluble cerium inhibitor used in the present invention is from about 0.00005 weight percent (0.5 part per million) to about 0.01 weight percent of the total weight of the compound (100 parts per million). The preferred amounts of phenolic type inhibitors used in the present invention is from about 0.001 weight percent (10 parts per million) to about 0.1 weight percent of the total compound (1000 parts per million).

Any type of cerium compound which is soluble in the ethylenically unsaturated organic compound can be used as a part of the inhibitor in this invention. Suitable cerium compounds include, among others: ceric ammonium nitrate, cerous acetate, cerous ammonium nitrate, cerous ammonium sulfate, cerous benzoate, cerous nitrate, cerous oxalate and the like.

The term "phenolic type inhibitor" as used herein includes those known inhibitors for ethylenically unsaturated organic polymerizable compounds such as acrylic acid. These inhibitors include dihydroxybenzene derivatives such as hydroquinone, catechol, resorcinol, dihydroxyxylene; methoxyphenols such as guaiacol and p-methoxyphenol; pyrogallol, methyl pyrogallol, cresols, phenol, xylenols 4,4-thiobis-6-tertiary butyl-3-methyl phenol and the like.

The combination of soluble cerium compounds and the phenolic type stabilizers provide a synergistic effect in inhibiting the ethylenically unsaturated organic compounds capable of addition polymerizing in that smaller amounts of inhibitor compared to standard inhibitors can be used to stabilize the ethylenically unsaturated organic compounds. A distinct advantage of the combination of inhibitors used in this invention is that the ethylenically unsaturated organic compounds containing these inhibitors can be readily distilled with insignificant amounts of polymers produced during distillation. Furthermore, the cerium ions present in the stabilized organic compounds can be readily removed or reduced if desired, by the use of ion exchange resins well known in the art for removal of metal ions.

The ethylenically unsaturated organic compound capable of addition polymerization which can be stabilized against unintentional or premature polymerization using the soluble cerium compounds as inhibitors include: acrylic acid, methacrylic acid, vinyl acetate, styrene, acrylonitrile, vinyl chloride, acrylamide, N-methylolacrylamide, glycidyl methacrylate, and the like; an alkyl acrylate ester wherein the alkyl group contains from 1 to 10 carbon atoms such as methyl acrylate, ethyl acrylate, n-butyl acrylate, octyl acrylate, isoctyl acrylate, 2-ethylhexyl acrylate and the like; an alkyl methacrylate ester wherein the alkyl group contains from 1 to 10 carbon atoms such as methyl methacrylate, ethyl methacrylate, butyl methacrylate, and the like; an acrylate ester prepared by the reaction of acrylic acid and a saturated aliphatic polyol having 2 to 10 carbon atoms and 2 to 5 hydroxy groups, said ester containing 2 to 5 acrylate groups such as pentaerythritol triacrylate, trimethyl propane, triacrylate, 1,6-hexandiol diacrylate, tetraethylene glycol diacrylate, tripropylene glycol diacrylate and trimethylol propane trimethacrylate and the like.

This invention will be further described in the following examples:

EXAMPLES 1-13

Glacial acrylic acid was redistilled to obtain acrylic acid without any inhibitor. To each 800 grams sample of uninhibited acrylic acid, 0.04 gram of inhibitor was added to provide 50 parts per million of inhibitor in the acrylic acid. In each acrylic sample, the following inhibitors were added: hydroquinone, catechol, p-methoxyphenol and guaiacol (o-methoxy phenol). Cerium compounds such as cerous acetate, ceric ammonium nitrate and ceric sulfate were added to the above acrylic acid samples containing the inhibitors to achieve a sample having 5 parts per million of cerium. For instance, 0.9919 gram cerous acetate hydrate [Ce(OAC)$_3$.1½H$_2$O] was dissolved in 400 grams water. This solution contained 1009 parts per million cerium. Fifty microliters of the cerium water solution was added to 10 milliliters inhibited acrylic acid to achieve 5 parts per million of cerium. Ten milliliter samples of each acrylic acid sample were placed in a test tube which was placed in a bath maintained at 100° C. The samples were timed to determine at what point initial polymerization of the acrylic acid occurs. This time is called the induction time. The following results were obtained:

| Examples | Content | Induction Time Hours |
|---|---|---|
| 1 | uninhibited acrylic acid | 1.1 |
|   |   | 14.8 |
| 2 | acrylic acid + 50 ppm p-methoxyphenol | 38 |
|   |   | 6.0 |
| 3 | acrylic acid + 50 ppm p-methoxyphenol + 5 ppm Ce$^{+4}$ (ceric ammonium nitrate) | 106.9 99-163 |
| 4 | acrylic acid + 50 ppm p-methoxyphenol + 5 ppm Ce$^{+3}$ (cerous acetate) | 117.3 91.7 |
| 5 | acrylic acid + 50 ppm hydroquinone | 1.1 33.9 |
| 6 | acrylic acid + 50 ppm hydroquinone + 5 ppm Ce$^{+4}$ (ceric ammonium nitrate) | 243-330 243-330 |
| 7 | acrylic acid + 50 ppm hydroquinone + 5 ppm Ce$^{+3}$ (cerous acetate) | 288 288 |
| 8 | acrylic acid + 50 ppm catechol | 0.8 18 |
| 9 | acrylic acid + 50 ppm catechol + 5 ppm Ce$^{+2}$ [Ce(SO$_4$)$_2$] (insoluble) in acrylic acid | <16 |
| 10 | acrylic acid + 50 ppm catechol + 5 ppm Ce$^{+4}$ (ceric ammonium nitrate) | 118.9 124 |
| 11 | acrylic acid + 50 ppm catechol + 5 ppm Ce$^{+4}$ (ceric ammonium nitrate) | 92.5 105.6 |
| 12 | acrylic acid + 50 ppm guaiacol + 5 ppm Ce$^{+4}$ (ceric ammonium nitrate) | 113.1 173.2 |
| 13 | acrylic acid + 50 ppm guaiacol + 5 ppm Ce$^{+3}$ (cerous acetate) | 151.5 379.5 |

In the above comparisons, Example 1, the uninhibited acrylic acid, had an induction time of from 1.1 to 14.8 hours. In every example where soluble cerium ions were present in combination with phenolic type inhibitors, much longer induction times were achieved than with samples without the cerium present. Of particular interest is Example 9 wherein cerous sulfate is not soluble in the acrylic acid and an induction period of less than 16 hours was obtained.

What is claimed is:

1. A composition of an ethylenically unsaturated organic compound capable of addition polymerization stabilized from premature polymerization in the liquid phase by the addition of stabilizing amounts of a combination of a cerium compound soluble in said ethylenically unsaturated organic compound and a phenolic type inhibitor, said ethylenically unsaturated organic compound being selected from the group consisting of acrylic acid, methacrylic acid, vinyl acetate, styrene, acrylonitrile, vinyl chloride, acrylamide, n-methylolacrylamide, glycidyl methacrylate, alkyl acrylate and methacrylate esters wherein the alkyl groups contain from 1 to 10 carbon atoms, and esters of acrylic acid and a saturated aliphatic polyol having 2 to 10 carbon atoms and 2 to 5 hydroxy groups, said esters each containing 2 to 5 acrylate groups.

2. The composition of claim 1 wherein the amount of cerium present is from about 0.1 part per million to about 5000 parts per million based on the total composition.

3. The composition of claim 2 wherein the amount of phenolic type inhibitor present is about 1 part per million to about 5000 parts per million based on the total composition.

4. The composition of claim 1 wherein the cerium compound is ceric ammonium nitrate.

5. The composition of claim 1 wherein the cerium compound is cerous acetate.

6. The composition of claim 1 wherein the phenolic type inhibitors are selected from the group consisting of hydroquinone, catechol, guaiacol and p-methoxyphenol.

7. The composition of claim 1 wherein the ethylenically unsaturated organic compound is acrylic acid.

8. The composition of claim 1 wherein the ethylenically unsaturated organic compound is methacrylic acid.

9. The composition of claim 1 wherein the ethylenically unsaturated organic compound is an alkyl acrylate ester wherein the alkyl group contains from 1 to 10 carbon atoms.

10. The composition of claim 9 wherein the alkyl acrylate is methyl acrylate.

11. The composition of claim 9 wherein the alkyl acrylate is ethyl acrylate.

12. The composition of claim 9 wherein the alkyl acrylate is butyl acrylate.

13. The composition of claim 1 wherein the ethylenically unsaturated organic compound is an acrylate ester and prepared by the reaction of acrylic acid and a saturated aliphatic polyol having 2 to 10 carbon atoms and 2 to 5 hydroxy groups, said acrylate ester containing 2 to 5 acrylate groups.

14. The composition of claim 13 wherein the acrylate ester is selected from the group consisting of pentaerythritol triacrylate, trimethylol propane triacrylate, 1,6-hexanediol diacrylate, tetraethylene glycol diacrylate, tripropylene glycol diacrylate, tripropylene glycol diacrylate and trimethylolpropane trimethacrylate.

15. The composition of claim 1 wherein the ethylenically unsaturated organic compound is styrene.

16. The composition of claim 1 wherein the ethylenically unsaturated organic compound is acrylamide.

* * * * *